United States Patent [19]

Thomas et al.

[11] Patent Number: 6,101,818
[45] Date of Patent: Aug. 15, 2000

[54] PROCESS FOR SEPARATING WATER FROM CHEMICAL MIXTURES

[75] Inventors: Raymond Hilton Percival Thomas, Niagara County; Rajiv Ratna Singh, Erie County; Jeffrey Warren McKown, Erie County; Roy Phillip Robinson, Erie County, all of N.Y.; Stephen Alan Cottrell, Baton Rouge, La.

[73] Assignee: AlliedSignal Inc., Morristown, N.J.

[21] Appl. No.: 08/967,632

[22] Filed: Nov. 10, 1997

[51] Int. Cl.⁷ .............................. F25B 47/00; B01D 3/00; C07C 17/10; C07C 17/38

[52] U.S. Cl. ................... 62/85; 62/475; 570/177; 570/262; 210/633

[58] Field of Search ............... 62/114, 85, 474, 62/475; 210/689, 502, 637; 570/262, 122, 177

[56] References Cited

U.S. PATENT DOCUMENTS

| | | | |
|---|---|---|---|
| 3,446,645 | 5/1969 | Drost | 117/29 |
| 3,625,866 | 12/1971 | Conde | 252/455 Z |
| 4,013,566 | 3/1977 | Taylor | 210/502 |
| 4,144,171 | 3/1979 | Krause | 210/496 |
| 4,220,553 | 9/1980 | Krause | 252/428 |
| 4,266,408 | 5/1981 | Krause | 62/474 |
| 4,447,565 | 5/1984 | Lula et al. | 523/219 |
| 4,777,232 | 10/1988 | Heidel . | |
| 4,828,710 | 5/1989 | Itoh . | |
| 4,985,467 | 1/1991 | Kelly et al. | 521/52 |
| 5,069,816 | 12/1991 | DeSantis et al. | 252/315.5 |
| 5,094,775 | 3/1992 | Bailey, Jr. | 252/182.24 |
| 5,149,334 | 9/1992 | Lahrman | 604/367 |
| 5,191,771 | 3/1993 | Meckler | 62/271 |
| 5,198,121 | 3/1993 | Masini et al. | 210/689 |
| 5,225,048 | 7/1993 | Yuan | 203/1 |
| 5,252,203 | 10/1993 | Lyda . | |
| 5,297,398 | 3/1994 | Meckler | 62/271 |
| 5,347,822 | 9/1994 | Lavin et al. | 62/85 |
| 5,440,898 | 8/1995 | Starr | 62/474 |
| 5,514,251 | 5/1996 | Balthasart | 203/14 |
| 5,514,633 | 5/1996 | Noguchi et al. | 502/64 |
| 5,534,186 | 7/1996 | Walker | 252/194 |
| 5,624,971 | 4/1997 | Wilson | 521/137 |
| 5,672,277 | 9/1997 | Parker et al. | 210/689 |
| 5,719,201 | 2/1998 | Wilson | 521/137 |

FOREIGN PATENT DOCUMENTS

| | | |
|---|---|---|
| 3093880 | 4/1991 | Japan . |
| 7033695 | 2/1995 | Japan . |
| 8173799 | 7/1996 | Japan . |
| 82006494 | 8/1996 | Japan . |
| 8206493 | 8/1996 | Japan . |
| W9241189 | 9/1997 | Japan . |

OTHER PUBLICATIONS

Section Ch, Week 8301, Derwent Publications Ltd., London, GB; AN 83–00758K XP002090715 & JP 57 187306 A (Sumitomo Chem. Co. Ltd.) Nov. 18, 1982.

*Primary Examiner*—William Doerrler
*Attorney, Agent, or Firm*—Colleen D. Szuch; Marie Collazo

[57] ABSTRACT

A method for separating water from a chemical mixture is provided. In the process of the invention, water is separated from a chemical mixture by contacting the chemical mixture with a water-soluble polymer.

24 Claims, No Drawings

PROCESS FOR SEPARATING WATER FROM CHEMICAL MIXTURES

FIELD OF THE INVENTION

The present invention relates to a method for drying chemical mixtures. More specifically, a method is provided for separating water from a water-containing chemical mixture by contacting the chemical mixture with a water soluble polymer.

BACKGROUND OF THE INVENTION

In a variety of manufacturing processes including, without limitation, halogenated hydrocarbon manufacturing processes, water may be present in the starting materials or formed during the reaction. In these processes, it may be desirable to separate the water from the process products, byproducts, and unreacted starting materials.

Additionally, in a number of technologies, such as electronics and semiconductor manufacturing, solvents may be used for drying manufactured parts. For the solvent to be re-usable, the water must first be removed.

Further, in refrigeration, air-conditioning, and freezing equipment, a refrigerant is used as the working fluid. Because these systems usually cannot be manufactured so as to totally exclude water from entering the final product, some water may mix with the working liquid in the equipment causing problems with the proper functioning of the equipment.

A number of methods have been developed in order to separate water from chemical mixtures. The known methods include the use of alkaline earth compounds, carbon molecular sieves, oleum, distillation, and membranes. Each of the known methods is disadvantageous in that these processes are inefficient or uneconomical. Also, water may be difficult to separate using these methods because water forms an azeotropic mixture with certain chemicals, such as some of the fluorinated hydrocarbons. Additionally, some drying methods result in undesirable side reactions between the drying agent and the material to be dried.

Many useful desiccants adsorb or absorb the fluid that is being dried as well as take up water from the fluid. This is exemplified in the adsorption of difluoromethane by 4 Å molecular sieves as described in U.S. Pat. No. 5,347,822.

Therefore, a need exists for an effective water separation method that attempts to overcome the disadvantages of the prior art methods.

DESCRIPTION OF THE INVENTION AND PREFERRED EMBODIMENTS

This invention provides a continuous, intermittent, or batch process for drying water-containing chemical mixtures. The process of the invention provides a convenient and cost-effective method for carrying out such drying.

The process of the invention comprises contacting a chemical mixture comprising water and at least one inorganic material organic material, or mixtures thereof with a drying effective amount of a drying agent comprising a water-soluble polymer. The process may also provide for recovering the water from the polymer for reuse and regeneration of the polymer.

For purposes of this invention, a chemical mixture is a liquid, gaseous or partially gaseous mixture of water and the at least one inorganic material, organic material, or mixtures thereof. Illustrative inorganic materials include, without limitation, hydrogen, hydrogen chloride, sulfur dioxide, sulfur trioxide, carbon monoxide, carbon dioxide, boron trifluoride, uranium hexafluoride, sulfur hexafluoride, arsenic pentafluoride, halide salts, nitric acid, sulfuric acid, chlorine, metal ions, non-aqueous inorganic solvents, and mixtures thereof. Exemplary organic material includes, without limitation, hydrocarbons, halogenated hydrocarbons such as chlorofluorocarbons, hydrochlorofluorocarbons, hydrofluorocarbons, and perfluorocarbons, chlorocarbons, hydrochlorocarbons, hydrofluoroethers, fluoroethers, and mixtures thereof, including without limitation difluoromethane, pentafluoropropane, tetrafluoroethane, and the like.

The process of the invention may be carried out in any suitable vessel. In the process of the invention, the chemical mixture is contacted with the water-soluble polymer for at least about 0.1 seconds, more preferably from about 0.1 to about 100,000 seconds, still more preferably from about 1 to about 10,000 seconds, and most preferably from about 2 to about 100 seconds.

For purposes of this invention, "polymer" may be a homopolymer, copolymer, or mixtures thereof. Generally, the polymers used in the invention have molecular weights of from about 5,000 to about 10,000,000. Preferably, polymers with molecular weights of from about 5,000 to about 1,000,000 are used. By "water-soluble polymer" is meant any high molecular weight compound that swells, to about twice its dry volume, or dissolves with the addition of water at room temperature.

Water-soluble polymer is meant to include semi-synthetic water-soluble polymers, synthetic water-soluble polymers, and mixtures thereof. Semi-synthetic water-soluble polymers are natural water-soluble polymer derivatives. Synthetic water-soluble polymers are not natural water-soluble polymer derivatives and are formed only through chemical reactions.

Exemplary semi-synthetic water-soluble polymers include, without limitation, cellulose ethers, modified starches, starch derivatives, natural gum derivatives, and mixtures thereof. Illustrative synthetic water-soluble polymers include, without limitation, polymers, related polymers, and polymer salts of acrylamide, acrylic acid, ethylene oxide, methacrylic acid, polyethyleneimine, polyvinyl alcohol, polyvinyl pyrrolidone, and mixtures thereof. By related polymer is meant that the polymer repeat unit, or a branch thereof, is extended by carbon atoms, preferably from one to four carbon atoms. For example, a related polymer of acrylic acid is one in which the vinyl group is extended by one carbon to form an allyl group.

Preferably, a synthetic water-soluble polymer is used. More preferably, polyacrylic acid or one of its salts is used. Most preferably, the water-soluble polymer is sodium polyacrylate.

The polymer may be selected in order to separate water alone. Alternatively, it may be selected so as to separate water and any other material from the chemical mixture.

In order to separate sufficient water from the chemical mixture so that only about 10 ppm or less of water remains, it may be necessary to use an essentially anhydrous water-soluble polymer. In such a case, the polymer may be dried by any convenient method. For example, the polymer may be dried by heating to a temperature of about 50° C. to about 250° C. for a period of about 30 minutes to about 48 hours. The requisite initial dryness of the water-soluble polymer used in the processes of the invention will depend on such factors as the amount of water in the chemical mixture to be dried, the amount of polymer used, and the equilibrium concentration of water in the polymer when it is in contact with the material at its final, or desired, water content.

Preferably, the water-soluble polymer is dried to the greatest extent possible prior to use. For example, the polymer may be heated in a vacuum desiccator to about 100 to about 200° C. and weighed periodically. As the polymer loses water, its weight decreases until it reaches a constant weight. At this point, the polymer has been dried to the greatest extent possible at that particular temperature.

The form of the polymer may be tailored for use with the process that produces the chemical mixture or in which the chemical mixture is being used. The amount of polymer used is a drying effective amount, which is readily determinable by consideration of the amount of water sought to be separated, the flow rate of the chemical mixture, and the adsorptive or absorptive characteristics of the polymer.

In one embodiment of the invention, the polymer is in the form of powder, fine particles, fibers, or a shaped piece or pieces and is placed in a vessel to form a packed bed. The chemical mixture is contacted with the polymer by passing the mixture through the vessel.

In another embodiment, the water-soluble polymer is used as a drying agent in equipment or a system that uses a refrigerant, such as in a refrigeration or air-conditioning unit. Refrigerants used in such systems and equipment are well known in the art and include halogenated hydrocarbons and azeotropic mixtures and blends thereof. Thus, the invention includes a process comprising the cycling of a refrigerant in a system wherein the refrigerant is condensed and thereafter evaporated, the system having a drying agent therein comprising the water-soluble polymer.

In this application, the physical form of the polymer is selected to be compatible with the requirements of the equipment and/or other drying material with which it may be used. The shape and hardness of the polymer should be chosen so as to be able to withstand the rigors of the system in which it is used.

The water-soluble polymer may be used alone or in combination with other drying agents. Typical drying agents include, without limitation, molecular sieves, such as zeolite sieves, activated alumina, and mixtures thereof. The water-soluble polymer and other drying agents preferably are formed so as to avoid entrainment in the equipment stream, plugging equipment openings and conduits. Thus, formation may be by any convenient method such as compaction. Alternatively, a binder material may be used. Suitable binder materials include, without limitation, clays, such as kaolin, wood node-type, attapulgite, and the like.

For example, a drier using the drying agent of the invention may be composed of packed polymer held together between porous metal plates. The polymer may be deposited on support made of cellulose or other suitable material. Alternately, the packed polymer may be in bead form and held together by a binding material. This packed polymer is the drier core and may be set in a container, the core and the container constituting the drier. The drier may then be used in the equipment in which separation of water from a fluid, such as a refrigerant is desired.

In yet another embodiment, the invention may be used in a process for producing halogenated hydrocarbons. Thus, the invention may include a process for producing halogenated hydrocarbons comprising contacting a chemical mixture comprising at least one halogenated hydrocarbon and water with a drying agent comprising a water-soluble polymer. In such a process the polymer may be used alone or in combination with other drying agents including, without limitation, anhydrous metal sulfates, chlorides, zeolites, and perchlorates, phosphorous pentoxide, and mixtures thereof.

In all embodiments, the performance of the polymer may be improved by periodically regenerating the polymer to release the water separated from the chemical mixture. Regeneration may be accomplished by any convenient means, such as by heating the polymer to a temperature suitable to release water from the polymer.

The amount of water removed by the polymer must be controlled in order to maintain the mechanical integrity of the polymer. If the polymer is in solid form, allowing the amount of water separated from the chemical mixture by the polymer to reach a level at which the polymer turns from a solid into a gel or liquid may be disadvantageous. The amount of water at which this phase change occurs will vary depending on the polymer used. Preferably, water separation is carried out up to the amount at which a phase change occurs. Water separation may be monitored by any convenient means as for example, measuring the amount of water in the chemical mixtures. Further, if one or more other chemicals in the chemical mixture forms a gel or solid with the polymer, the water required for the solid to liquid phase change may be altered. It is preferred that only the water is adsorbed or absorbed by the polymer.

If very low levels of water are desired in the chemical mixture, that mixture may be treated sequentially with more than one polymer bed to reach the desired level. Alternatively, the process of the invention may be used in conjunction with one of the well known drying methods.

The invention will be clarified further by a consideration of the following examples that are purely exemplary.

EXAMPLES

Example 1

A sample of HFC-245ca was loaded with water to a concentration of 1485 ppm. The potassium salt of polyacrylic acid was dried to 469 ppm in an oven. 0.18 g potassium salt of the polyacrylic acid was then added to 28.4 g of wet HFC-245ca, the weight of the polyacrylic acid being 0.6% of the weight of the HFC-245ca. After standing for 20 minutes, the water concentration in the HFC-245ca was 898 ppm. The weight of the polyacrylic acid salt was then increased to 0.98 g, 3.5 wt % of the HFC-245ca. After another 30 minutes, the water concentration of the HFC-245ca was found to be 255 ppm. Thus, in one hour, the water content of the HFC-245ca was reduced by 83% using a maximum of 3.5 wt % of the polymer. After 2 days, the moisture level dropped to 95 ppm, or 94%.

Example 2

4 g water were added to 907 g of HCFC-141b. To this mixture was added 10 g AW-300 molecular sieve, 1.1% of the weight of the HCFC-141b, and 8 g, of the dried sodium salt of polyacrylic acid, 0.9 wt % of the HCFC-141b. The AW-300 molecular sieve was activated in an oven at 500° C. for 6 hours. The water capacity for AW-300 is 10 g per 100 g of sieve. Thus, the molecular sieve should be able to remove 1 g of water from the HCFC-141b. One hour after adding the drying agents, the water content of the HCFC-141b was 248 ppm. 0.225 g of water remained in the HCFC-141b and 3.775 g had been removed, the acid salt of the polyacrylic acid removing 2.775 g.

Example 3

80.03 g HCFC-141b containing 2000 ppm water were prepared. To that mass of HCFC-141b, 16 g dried sodium salt of polyacrylic acid were added and the mixture stirred. Moisture content was then measured as a function of time and the results are shown on Table 1.

TABLE 1

| Time (hrs) | Water Concentration (ppm) |
|---|---|
| 0.0 | 2000 |
| 0.5 | 57 |
| 1.0 | 40 |
| 1.5 | 32 |
| 2.0 | 30 |
| 4.0 | 30 |
| 23.5 | 19 |

The results demonstrate that the moisture level was reduced from 2000 ppm to 57 ppm in 30 min. and to 19 ppm in about 24 hours.

Example 4

80.0 g HCFC-141b containing 2000 ppm water were prepared, To that mass of HCFC-141b, 8 g of the dried sodium salt of polyacrylic acid were added and the mixture stirred. The moisture level was the measured as a function of time. The results are shown on Table 2.

TABLE 2

| Time (hrs) | Water Concentration (ppm) |
|---|---|
| 0.0 | 2000 |
| 0.5 | 53 |
| 1.0 | 50 |
| 2.0 | 48 |
| 4.0 | 37 |

The results show that the moisture level was reduced from 2000 ppm to 53 ppm in 30 minutes and finally to 37 ppm in four hours.

Example 5

80.0 g HCFC-141b containing 2000 ppm water were prepared, To that mass of HCFC-141b, 4 g of the dried sodium salt of polyacrylic acid were added and the mixture stirred. The moisture level was the measured as a function of time. The results are shown on Table 3.

TABLE 3

| Time (hrs) | Water Concentration (ppm) |
|---|---|
| 0.0 | 2000 |
| 0.5 | 76 |
| 1.0 | 40 |
| 2.5 | 59 |
| 24.0 | 29 |

The results show that the moisture level was reduced from 200 ppm to 29 ppm in 24 hours.

Example 6

100.0 g HCFC-141b containing 2000 ppm water were prepared, To that mass of HCFC-141b, 0.05 g of the dried sodium salt of polyacrylic acid were added and the mixture stirred. The moisture level was the measured as a function of time. The results are shown on Table 4.

TABLE 4

| Time (hrs) | Water Concentration (ppm) |
|---|---|
| 0.0 | 2000 |
| 1.0 | 275 |
| 24.0 | 252 |

The results show that the moisture level was reduced from 2000 ppm to 252 ppm in 24 hours. The sodium salt of the polyacrylic acid absorbed 40 times its weight in water fro the HCFC-141b and was in equilibrium with HCFC-141b that contained a water concentration of 252 ppm.

Example 7

5.4 g of the dried sodium salt of polyacrylic acid were placed in a 40 cc stainless steel cylinder. The cylinder was evacuated and 30.5 g difluoromethane were added to the cylinder. Initially, the difluoromethane contained 302 ppm water. After letting the cylinder sit overnight, the water content of the difluoromethane was measured as being less than 1 ppm.

What is claimed is:

1. A process comprising the step of contacting a chemical mixture comprising water and at least one, halogenated hydrocarbon with a drying agent comprising a water-soluble polymer.

2. The process of claim 1 wherein the halogenated hydrocarbon comprises difluoromethane.

3. The process of claim 1 wherein the water-soluble polymer is a synthetic water-soluble polymer.

4. The process of claim 3 wherein the synthetic water-soluble polymer is polyacrylic acid or a salt of polyacrylic acid.

5. The process of claim 4 wherein the polymer is sodium polyacrylate.

6. A process comprising the step of contacting a chemical mixture comprising water and difluoromethane with a drying agent comprising sodium polyacrylate.

7. A process comprising the steps of cycling a refrigerant in a system wherein the refrigerant is condensed and thereafter evaporated, the system having therein a drying agent comprising a water-soluble polymer.

8. The process of claim 7 wherein the drying agent further comprises at least one of the group consisting of molecular sieves, activated alumina, and mixtures thereof.

9. The process of claim 7 wherein the drying agent further comprises a zeolite molecular sieve.

10. The process of claim 7 wherein the drying agent further comprises activated alumina.

11. The process of claim 7 wherein the drying agent further comprises a zeolite molecular sieve and activated alumina.

12. A process for producing halogenated hydrocarbons comprising the step of contacting a chemical mixture comprising water and at least one halogenated hydrocarbon with a drying agent comprising a water-soluble polymer.

13. The process of claim 12 wherein the drying agent further comprises at least one of the group consisting of anhydrous metal sulfates, chlorides and perchlorates, phosphorous pentoxide, and mixtures thereof.

14. The process of claim 1 where said halogenated hydrocarbon is selected from the group consisting of chlorofluorocarbons, hydrochlorofluorocarbons, hydrofluorocarbons, perfluorocarbons, chlorocarbons, hydrochlorocarbons, hydrofluoroethers, difluoroethers and mixtures thereof.

15. The process of claim 14 wherein said halogenated hydrocarbon is a hydrofluorocarbon.

16. The process of claim 15 wherein said hydrofluorocarbon is selected from the group consisting of difluoromethane, pentafluoropropane, tetrafluoroethane and mixtures thereof.

17. The process of claim 1 wherein the water-soluble polymer is selected from the group consisting of semi-synthetic water soluble polymers, synthetic water-soluble polymers and mixtures thereof.

18. The process of claim 3 wherein the polymer comprises poly(methyl methacrylate).

19. The process of claim 3 wherein the polymer comprises potassium polyacrylate.

20. A process comprising contacting a chemical mixture comprising water and difluoromethane with a drying effective amount of potassium polyacrylate.

21. The process of claim 1 wherein the polymer is regenerated subsequent to use.

22. The process of claim 21 wherein water is recovered from the regenerated polymer.

23. The process of claim 1 wherein the polymer is used in combination with a second drying agent.

24. The process of claim 23 wherein the second drying agent is selected from the group consisting of molecular sieves, activated alumina and mixtures thereof.

* * * * *